(12) United States Patent
Barmaimon et al.

(10) Patent No.: US 10,905,821 B2
(45) Date of Patent: Feb. 2, 2021

(54) CAPACITOR DETECTION FOR IV PUMP TUBE CALIBRATION

(71) Applicants: Eyal Barmaimon, Haifa (IL); Lior Shtram, Haifa (IL); Shai Finkman, Haifa (IL); Elie Yaacobi, Haifa (IL); Ronny Bellan, Nazareth (IL); Nadav Cohen, Haifa (IL); Amit Schnell, Kiryat Tivon (IL)

(72) Inventors: Eyal Barmaimon, Haifa (IL); Lior Shtram, Haifa (IL); Shai Finkman, Haifa (IL); Elie Yaacobi, Haifa (IL); Ronny Bellan, Nazareth (IL); Nadav Cohen, Haifa (IL); Amit Schnell, Kiryat Tivon (IL)

(73) Assignee: Flex, Ltd., Singapore (SG)

( * ) Notice: Subject to any disclaimer, the term of this patent is extended or adjusted under 35 U.S.C. 154(b) by 263 days.

(21) Appl. No.: 16/032,527

(22) Filed: Jul. 11, 2018

(65) Prior Publication Data

US 2020/0016325 A1 Jan. 16, 2020

(51) Int. Cl.
*A61M 5/142* (2006.01)
*A61M 5/168* (2006.01)
(Continued)

(52) U.S. Cl.
CPC .......... *A61M 5/142* (2013.01); *A61M 5/1685* (2013.01); *A61M 5/16877* (2013.01);
(Continued)

(58) Field of Classification Search
CPC .. A61M 5/142; A61M 5/172; A61M 5/16877; A61M 5/1685;
(Continued)

(56) References Cited

U.S. PATENT DOCUMENTS

| 2,791,657 A | 5/1957 | Bloxsom et al. |
| 3,563,090 A | 2/1971 | Deltour |

(Continued)

FOREIGN PATENT DOCUMENTS

| DE | 690 07 342 T2 | 9/1994 |
| EP | 0 390 388 A2 | 10/1990 |

(Continued)

*Primary Examiner* — Bhisma Mehta
*Assistant Examiner* — Daniel Moore
(74) *Attorney, Agent, or Firm* — Volpe Koenig

(57) ABSTRACT

A system and method for calibrating an IV pump infusion system tube comprises a fluid source, an infusion system comprising, an IV pump, a drive unit, a chamber with known constant volume, a control unit, and IV tubing with a known inner diameter tolerance, and a set of conductive plates. The system administers medicinal fluid, calculates the flow rate of the medicinal fluid in the chamber by measuring the time the capacitance level of the medicinal fluid changes from a capacitance level corresponding to a first (initial) position to a capacitance level corresponding to a second (filled) position, compares the calculated flow rate with a set flow rate of the IV pump input in the control unit prior to infusion, and adjusts the IV pump and flow rate based on the compared deviations for more accurate delivery to a patient. This configuration may therefore provide a more precise delivery rate.

8 Claims, 3 Drawing Sheets

(51) Int. Cl.
*A61M 5/172* (2006.01)
*A61B 5/1495* (2006.01)
(52) U.S. Cl.
CPC ............ *A61M 5/172* (2013.01); *A61B 5/1495* (2013.01); *A61M 5/16804* (2013.01); *A61M 2005/14208* (2013.01); *A61M 2005/16863* (2013.01)
(58) Field of Classification Search
CPC ......... A61M 2005/16863; A61M 2005/14208; A61M 5/16804; A61M 5/16886; A61M 2005/1402; A61M 2205/3396; A61M 2205/3341; A61M 2205/3334; A61M 2205/3317; A61B 5/1495
See application file for complete search history.

(56) References Cited

U.S. PATENT DOCUMENTS

| | | |
|---|---|---|
| 3,635,678 A | 1/1972 | Seitz et al. |
| 3,942,526 A | 3/1976 | Wilder et al. |
| 4,954,046 A | 9/1990 | Irvin et al. |
| 5,215,450 A | 6/1993 | Tamari |
| 8,343,093 B2 | 1/2013 | Rush |
| 8,496,613 B2 | 7/2013 | Zhou |
| 8,839,681 B2 | 9/2014 | Stewart et al. |
| 2005/0238497 A1 | 10/2005 | Holst et al. |
| 2009/0259199 A1 | 10/2009 | Lampropoulos |
| 2009/0319204 A1* | 12/2009 | Brown .................. A61M 5/365 702/47 |
| 2010/0121257 A1* | 5/2010 | King .................. A61M 1/0058 604/22 |
| 2010/0126268 A1* | 5/2010 | Baily .................. A61M 1/0001 73/304 C |
| 2010/0211003 A1 | 8/2010 | Sundar et al. |
| 2010/0225494 A1 | 9/2010 | Thorpe |
| 2011/0282277 A1 | 11/2011 | Kim |
| 2012/0305090 A1 | 12/2012 | Bene |
| 2013/0201482 A1* | 8/2013 | Munro ................ A61M 5/1689 356/407 |
| 2014/0171869 A1* | 6/2014 | Zhang ............... A61M 5/16831 604/111 |
| 2014/0263063 A1* | 9/2014 | Jones ................ G01R 33/1276 210/647 |
| 2015/0057613 A1 | 2/2015 | Clemente |
| 2015/0290392 A1* | 10/2015 | Henderson .......... A61M 5/3204 604/111 |
| 2017/0146381 A1* | 5/2017 | Eckel ............... A61M 5/31535 |
| 2018/0064871 A1 | 3/2018 | James |

FOREIGN PATENT DOCUMENTS

| | | |
|---|---|---|
| WO | 2014/052997 A1 | 4/2014 |
| WO | 2015/007595 A | 1/2015 |
| WO | 2017021229 A1 | 2/2017 |

* cited by examiner

CAPACITOR DETECTION FOR IV PUMP TUBE CALIBRATION

CROSS REFERENCE TO RELATED APPLICATION

This application is related to the following commonly owned, co-pending, United States patent applications, the disclosures of which are incorporated by reference herein: U.S. patent application. Title "VISUAL DETECTION FOR IV PUMP TUBE CALIBRATION" to Barmaimon, et al., which was filed concurrently with this application on Jul. 11, 2018; U.S. patent application. Title "REED SWITCH DETECTION FOR IV PUMP TUBE CALIBRATION" to Barmaimon et al., which was filed concurrently with this application on Jul. 11, 2018.

SUMMARY

A system and method for calibrating flow rate of an IV pump infusion system comprising a fluid source, an infusion system comprising a control unit, an IV pump, a drive unit, and a chamber with known constant volume comprising an inlet on one side and a lower outlet on the opposite side, and IV tubing with a known inner diameter tolerance configured to operatively couple the fluid source to the inlet of the chamber, and the outlet of the chamber to a patient, and conductive plates that measure the capacitance of threshold height levels. The control unit is configured to operate the drive unit, and further configured to measure the amount of time the medicinal fluid takes to rise from a first (initial) position to a second (filled) position of the chamber using the conductive plates, calculate the flow rate of the medicinal fluid in the chamber, compare the calculated flow rate with a pre-set flow rate of the IV pump input into the control unit prior to infusion, and adjust the IV pump and flow rate based on the compared deviation.

BRIEF DESCRIPTION OF THE DRAWINGS

The present invention is illustrated by way of example, and not by way of limitation, in the figures of the accompanying drawings in which.

DETAILED DESCRIPTION OF THE PREFERRED EMBODIMENTS

Intravenous ("IV") infusion is a popular type of therapy that efficiently delivers liquid substances to a patient directly through a vein. IV infusion is necessary for the treatment of a variety of broad ranging diseases, conditions, and symptoms. The infusion system, delivery method, and flow and dosage details are therefore imperative in determining effective drug administration and therapy.

IV pumps play a crucial role in delivering fluids and complex doses of medications to patients in a wide range of care settings. Currently, medications and pharmaceutical drugs administered through the IV pump attempt to infuse at a smooth and continuous flow rate that is input into the infusion system prior to infusion. Delivery accuracies, however, greatly vary. IV pump inaccuracies typically result from the disposable infusion systems used.

One reason for inaccuracies in infusion systems is because the systems have a common tube inner diameter tolerance of ±0.05 mm. This variance of inner diameter tolerance causes the volume of substance being delivered through the IV infusion system to be determined by the actual inner diameter. As a result, drug delivery to a patient may not be precise and could result in harm to the patient or wasting of the medication or substance to be administered.

It would therefore be beneficial to offer an IV infusion system with flow or volume measurement calibration that calculates the flow rate of a medicinal substance and adjusts the infusion system according to any deviations found, to help improve substance-delivery accuracy.

Figure 1:
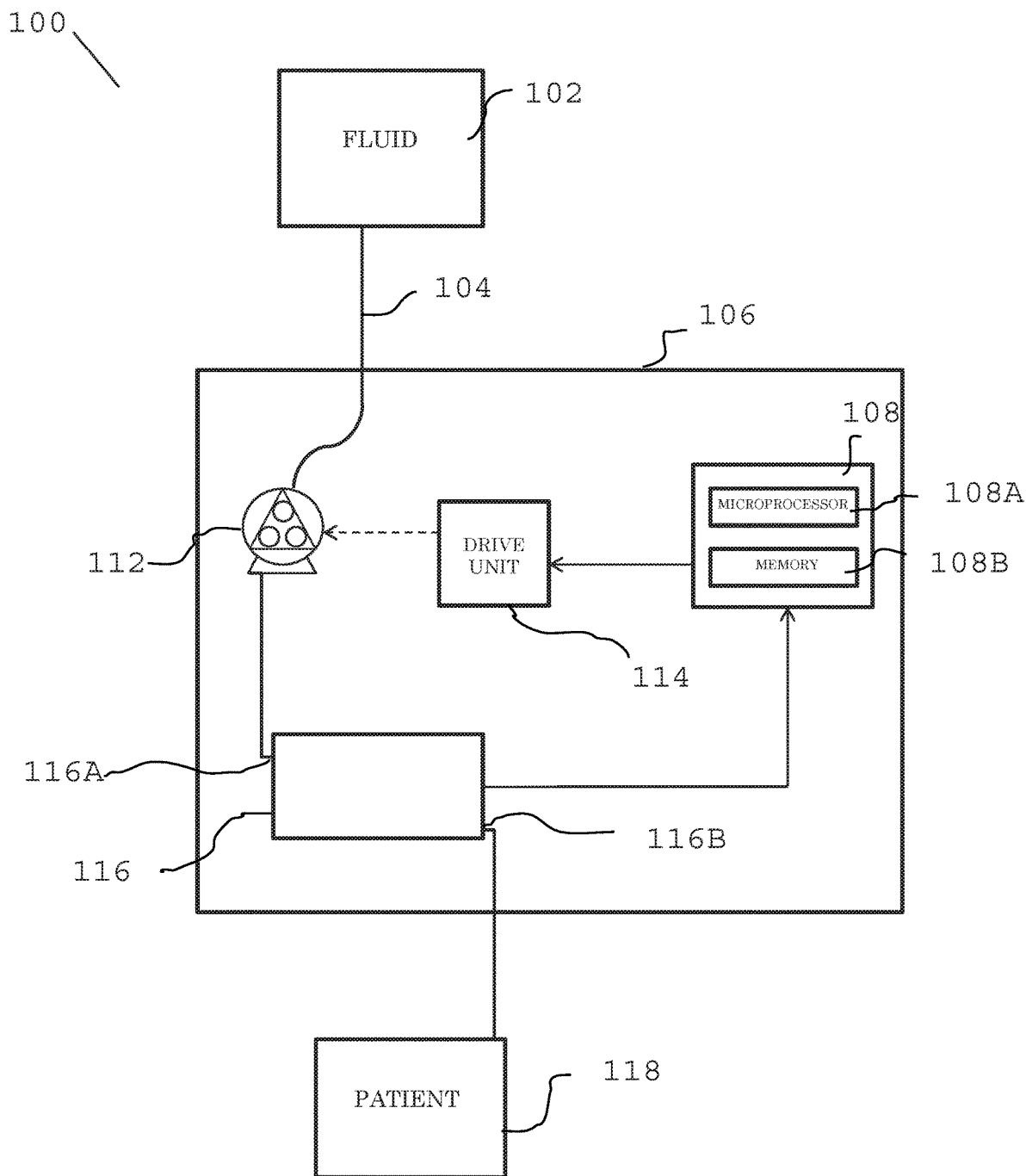
FIG. 1 is a schematic block diagram of an IV infusion flow rate calibration system.

FIG. 1 is a schematic block diagram of an IV infusion and calibration system 100 in accordance with the teachings herein. The infusion and calibration system 100 comprises a fluid source 102, IV tubing 104, and an infusion system 106. The infusion system 106 may include a control unit 108, an IV pump 112, a drive unit 114, and a calibration chamber 116.

In the present embodiment as described hereinafter, the calibration chamber 116 may be used in IV infusion therapies, and for purposes of explanation, the IV infusion and calibration system 100 will be described with reference to IV infusion. However, those of skill in the art would realize that in other embodiments, the calibration chamber 116 may be used to perform other therapeutic or diagnostic procedures. During IV infusion, a practitioner may use an IV pump to deliver a precise amount of medicinal fluid into a patient's vein over a controlled period of time. Linear peristaltic pumps are typically used in order to maintain sterilization of the IV infusion system. These pumps require a peristaltic apparatus that occludes a resilient IV tube through which the IV fluid is pumped. The tubing is compressed against a stationary plate and the compression and decompression regulate the desired flow. When the tubing occludes, the tubing forces the fluid to go through the patient's vessel at a pre-selected rate.

Current manufactured tubing for linear peristaltic IV pumps, however, vary slightly in inner diameter and outer diameter size. Consequently, these tubes have an inner diameter ("ID") tolerance of ±0.05 mm or more. This tolerance effect ultimately impacts the volume inside the tube. For example, the nominal volume of an IV tube is currently calculated using the following equation:

$$v_{nom} = \pi \times \frac{ID^2}{4} \times \Delta l \qquad \text{Equation (1)}$$

In contrast, the maximum volume of the IV tube, taking into consideration the +0.05 mm tolerance, is calculated as follows:

$$v_{max} = \pi \times \frac{(ID + 0.05)^2}{4} \times \Delta l \qquad \text{Equation (2)}$$

And the minimum volume of the IV tube, taking into consideration the −0.05 mm tolerance, is calculated as follows:

$$v_{max} = \pi \times \frac{(ID - 0.05)^2}{4} \times \Delta l \qquad \text{Equation (3)}$$

As a result, the current tolerance effect of IV tubing inner diameters provides approximately a ±3.5% change in volume inside the tube when using a tube with 3 mm ID, which is common in IV settings. Having a tube volume deviation of ±3.5% makes it difficult to effectively administer the precise amount of medicinal fluid over a specific time to a patient, since the volume inside the tubing varies. The inability to measure the exact flow rate of fluid inside the tubing without expensive in-line products also makes it difficult to combat the variance in administration due to tube volume deviation. As a result, the patient may be administered more or less medicine than the required dosage, which could ultimately harm the patient. Administering an excess dosage of medicinal fluid also unnecessarily wastes expensive medicine.

Returning to FIG. 1, in the present embodiment, the IV infusion and calibration system 100 calculates the flow rate of medicinal fluid using the chamber 116, during priming, and then compares the calculated flow rate with the input flow rate in the IV pump 112 in order to calibrate and adjust infusion for more accurate medicine delivery. The flow rate is calculated by measuring the amount of time the medicinal fluid rises inside the chamber 116 of the infusion system 106 from a first designated level to a second designated level.

Prior to infusion, a set rotational speed and equivalent flow rate for the IV pump 112 is input into the control unit 108. When infusion begins, the medicinal fluid stored in the fluid source 102 flows through the IV tubing 104 and to a patient 118. The control unit 108 may begin infusion by communicating with the drive unit 114 to operate the IV pump 112. The control unit 108 may comprise a microprocessor 108A and a memory 108B. In other embodiments, the control unit 108 may use other types of logic devices for driving the drive unit 114, such as a hardwired logic control, an application specific integrated circuit, etc. In one embodiment, the drive unit 114 may comprise an electrical motor to drive the IV pump 112. In the present embodiment, the IV pump 112 is a standard peristaltic pump. Accordingly, the IV tubing 104 is a standard manufactured tubing commonly used with peristaltic IV pumps, and thus has an ID tolerance of approximately ±0.05 mm.

As infusion continues, medicinal fluid stored in the fluid source 102 flows through the IV tubing 104 into the infusion system 106. In the embodiment set forth in the drawings and as described hereinafter, the fluid source 102 is an IV bag. However, that is just by way of example. In other embodiments, the fluid source 102 may be any sterilized container able to store the medicinal fluid. The medicinal fluid flows through the IV tubing 104 in the infusion system 106 and flows into the chamber 116. In the present embodiment, the chamber 116 is a cylindrical hollow thermoplastic chamber with an inlet 116A and an outlet 116B for the medicinal fluid to flow through. The chamber 116 has a constant pre-measured volume that is inputted into the control unit 108. As medicinal fluid flows into the chamber 116 via the inlet 116A, the control unit 108 determines the time it takes for the medicinal fluid to fill the chamber 116 by measuring the duration of the fluid rising from a specified first (initial) position in the chamber 116 to a specified second (filled) position in the chamber 116.

Several different mechanisms may be used to determine the fluid level and filling duration in the chamber 116. In one embodiment, the chamber 116 may comprise a detection mechanism. The detection mechanism may include a sterilized floating object in the chamber 116 and one or more imaging sensors that detects the rise of the medicinal fluid as the sterilized object floats and rises. In another embodiment, the chamber 116 may comprise a reed switch mechanism. The reed switch mechanism may comprise a floating magnetic object in the chamber 116 and an open reed switch along the outside of the chamber 116 that detects the rise of the fluid when the magnetic ball approaches and closes the switch. In yet another embodiment, the chamber 116 may comprise a capacitor mechanism. The capacitor mechanism may include conductive plates on the outside of the chamber 116 that determine the fluid level based on the changing capacitance of the fluid as it fills the chamber. In other embodiments, the fluid level and filling durations may be detected by a Hall Effect sensor in the chamber or various imaging sensor mechanisms.

The duration information for the rising medicinal fluid in the chamber 116 and the fluid levels in the chamber 116 are communicated to, and stored in, the control unit 108. In one embodiment, the chamber 116 may be communicatively connected to the control unit 108 through electrical wiring. In another embodiment, the chamber 116 may be communicatively connected to the control unit 108 wirelessly. The microprocessor 108A may comprise a general-purpose computer, with suitable front end and interface circuits for receiving signals from the chamber 116 and controlling the other components of the infusion system 106. The microprocessor 108A may be programmed in software to carry out the functions described herein. The software may be downloaded in electronic form, over a wired or wireless network, for example, or it may be provided on tangible media, such as optical, magnetic or electronic memory media. In other embodiments, some or all of the functions of the microprocessor 108A may be carried out by dedicated or programmable digital hardware components. The control unit 108 then calculates the flow rate of the medicinal fluid in the chamber 116 using the equation:

$$\text{Flow rate} = \frac{volume_{chamber}}{\Delta t} \qquad \text{Equation (3)}$$

Where $volume_{chamber}$ is the input volume of the chamber 116, and Δt is the time taken for the fluid to rise from the specified first (initial) position in the chamber 116 to the specified second (filled) position.

The control unit 108 may calculate the volume and flow rate of the medicinal fluid as it rises in the chamber 116. The control unit 108 may store the calculated flow rate values in the memory 108B. The control unit 108 may compare the calculated volume and flow rate of the medicinal fluid with the input rotational speed and equivalent flow rate of the IV pump 112 prior to infusion. If the calculated flow rate of the medicinal fluid deviates from the pre-set flow rate from the IV pump 112, the control unit 108 may communicate with the drive unit 114 and the IV pump 112 to calibrate the IV pump 112 to a rotational speed to achieve an accurate flow rate delivery. In one embodiment, the IV pump 112 may be communicatively connected to the control unit 108 through electrical wiring. In another embodiment, the IV pump 112 may be communicatively connected to the control unit 108 wirelessly. The control unit 108 and the drive unit 114 may adjust the IV pump 112 via the motor. The control unit 108 and drive unit 114 therefore adjusts the volume and flow rate based on the speed of the IV pump 112 to achieve the precise and required medicine delivery to the patient 118. The medicinal fluid leaves the chamber 116 via the outlet 116B and is then delivered into the patient 118 through additional IV tubing 104 with improved volume accuracy and flow rate.

Figure 2:
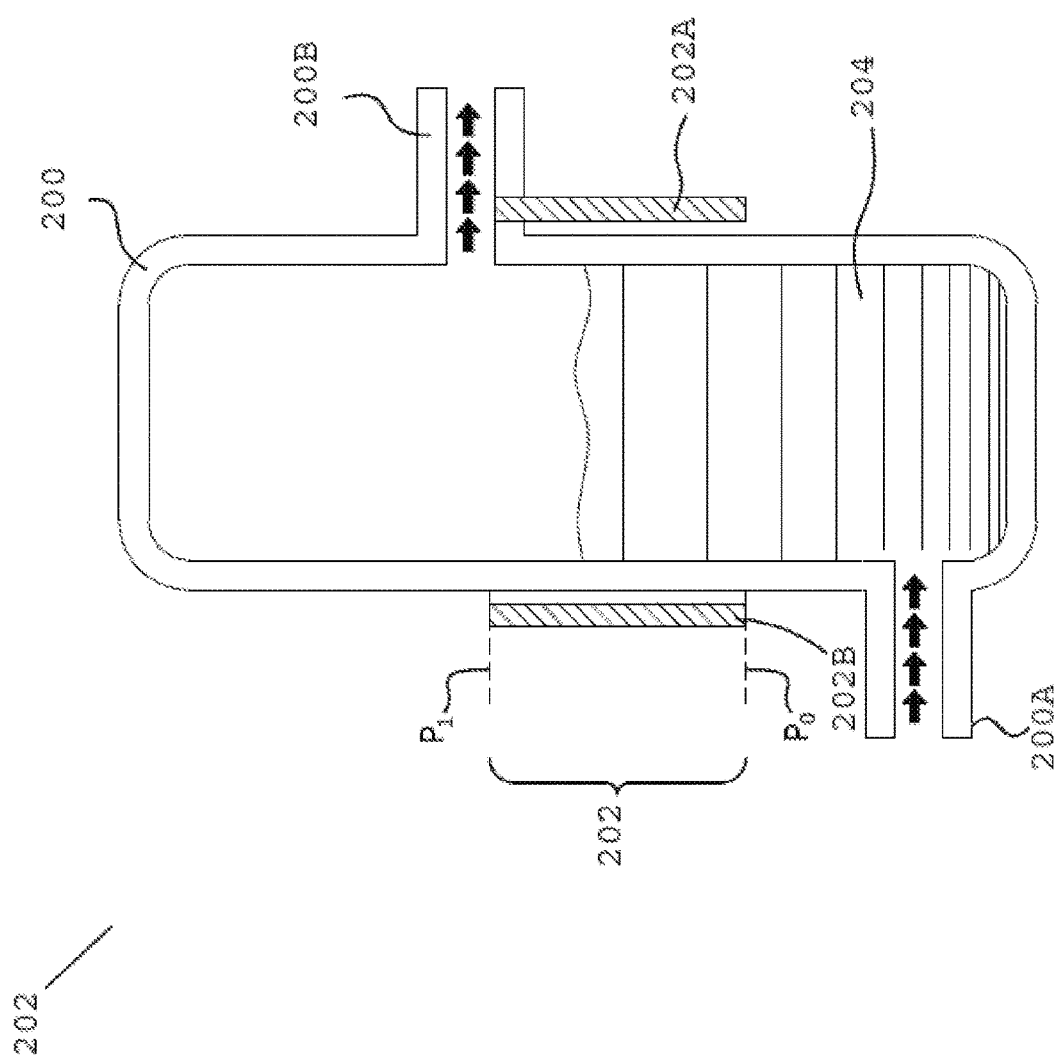
FIG. 2 is a diagram of a calibration system chamber with a capacitor mechanism.

FIG. 2 is a diagram of an IV infusion and calibration system chamber 200 with a capacitor mechanism 202. The chamber 200 has a known, constant volume. The chamber 200 includes an inlet 200A and an outlet 200B for medicinal fluid 204 to flow. The capacitor mechanism 202 comprises a set of conductive plates 202A and 202B. The conductive plates 202A and 202B may be disposed on an external portion of the chamber 200. The chamber 200 and the medicinal fluid 204 may form a dielectric that varies as the fluid level changes. As a result, the capacitance between the conductive plates 202A and 202B may vary accordingly.

The conductive plates 202A and 202B must be large enough to produce electric field lines through the chamber 200 and the medicinal fluid 204 and serve as the plates of a capacitor. In the embodiment set forth in the drawings and as described hereinafter, the conductive plates 202A and 202B may be a set of rectangular plates. However, that is just by way of example. In other embodiments, the conductive plates may be thin wires, circular dots or conductive coatings covering a portion of the chamber.

The conductive plates 202A and 202B may be connected to circuitry and may communicate with a control unit of the IV infusion and calibration system (not depicted) to determine fluid level based on the changing capacitance measured over a continuum. The capacitance detected by conductive plates 202A and 202B may be converted into an electric signal. This signal may be compared by a comparator with reference signals that correspond to the capacitance values of an initial filling position $P_0$ and a subsequent filled position $P_1$. As the capacitance changes, when the capacitance of the medicinal fluid 204 reaches a threshold value set by the reference level of the initial filling detection position $P_0$ of the chamber 200, the conductive plates 202A and 202B may communicate with the control unit (not depicted). The control unit may measure the time until capacitance reaches another threshold set by the reference level of the subsequent filled position $P_1$. The control unit may therefore measure and record this information and use the data to calculate the flow rate of the medicinal fluid in the chamber. The calculated flow rate may then be used to calibrate and adjust the IV pump infusion system for improved drug delivery accuracy.

Figure 3:
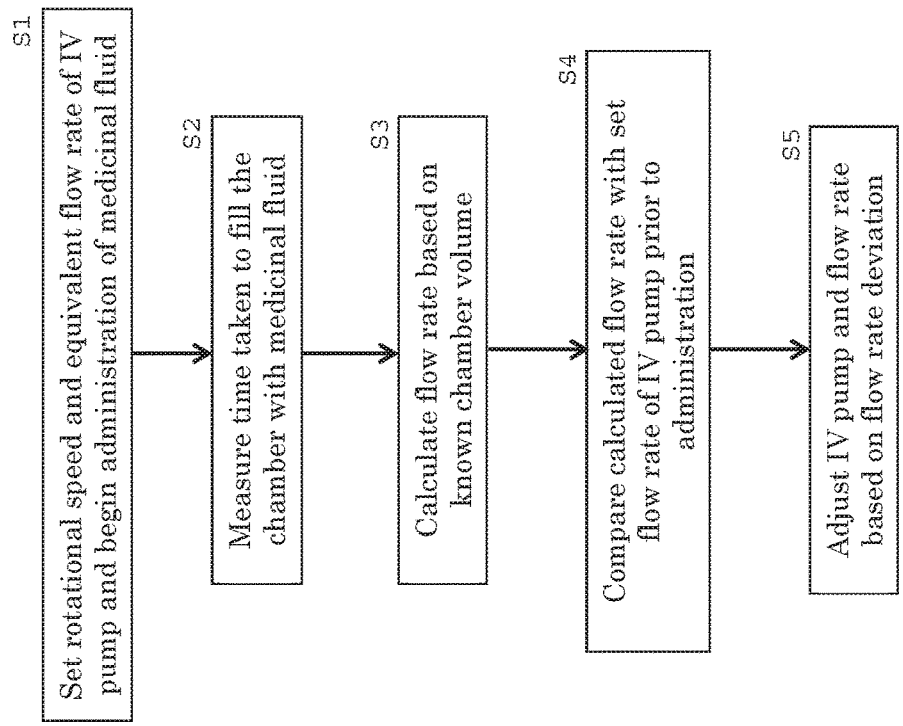
FIG. 3 is a simple flow diagram of a method of calibration for an IV pump infusion system.

FIG. 3 is a simple flow diagram of a method of flow rate measurement and calibration for an IV infusion system. A set rotational speed and equivalent flow rate of the IV pump is set and input into the infusion system. The medicinal fluid is released from a fluid source and enters the infusion system (S1). The IV infusion and calibration system measures the time it takes for the fluid to fill a chamber with a known, constant volume in the infusion system (S2). The system may measure this duration by determining the amount of time the fluid rises past two predetermined height positions using conductive plates detecting capacitance in the chamber. The capacitance detected by conductive plates may be converted into an electric signal, which may be compared by a comparator with reference signals that correspond to the capacitance values of the height positions.

The IV infusion and calibration system then calculates the flow rate of the medicinal fluid in the chamber (S3). Based on the calculated flow rate, the IV infusion and calibration system compares the calculated flow rate with the set flow rate of the IV pump (S4). As a result, the IV infusion and calibration system may calibrate and adjust the IV pump and flow rate based on the compared deviations in order to provide more accurate required dosage of medicine over a more precise duration (S5).

Having thus described the presently preferred embodiments in detail, it is to be appreciated and will be apparent to those skilled in the art that many physical changes, only a few of which are exemplified in the detailed description of the invention, could be made without altering the inventive concepts and principles embodied therein. It is also to be appreciated that numerous embodiments incorporating only part of the preferred embodiment are possible which do not alter, with respect to those parts, the inventive concepts and principles embodied therein. The present embodiments and optional configurations are therefore to be considered in all respects as exemplary and/or illustrative and not restrictive, the scope of the invention being indicated by the appended claims rather than by the foregoing description, and all alternate embodiments and changes to this embodiment which come within the meaning and range of equivalency of said claims are therefore to be embraced therein.

What is claimed is:

1. A calibration system for an IV pump infusion, comprising:
    a chamber with constant volume comprising an inlet and an outlet, and is configured to allow a medicinal fluid to enter via the inlet and exit via the outlet;
    two or more conductive plates coupled to the chamber and configured to measure an amount of time the medicinal fluid changes in capacitance level from a first capacitance level corresponding to a first position of the medicinal fluid in the chamber to a second capacitance level corresponding to a second position of the medicinal fluid in the chamber, and transmit this measurement to an IV pump control unit,
    wherein the medicinal fluid exits the chamber via the outlet when the medicinal fluid fills the chamber past the second position.

2. The calibration system according to claim 1, wherein the two or more conductive plates are coupled between the first position and the second position, and further configured to detect capacitance levels as the medicinal fluid rises.

3. The calibration system according to claim 2, wherein the IV pump control unit is further configured to convert the detected capacitance levels into electric signals and compare the electric signals with reference signals corresponding to the first position and the second position via a comparator.

4. The calibration system according to claim 1, wherein the IV pump control unit comprises:
    a microprocessor configured to:
        receive an input flow rate,
        calculate flow rate data of the medicinal fluid in the chamber based on the measured amount of time the capacitance level of the medicinal fluid changes from the first capacitance level to the second capacitance level, and
        compare the calculated data with the input flow rate; and
    a memory configured to store the calculated and compared data and the measured amount of time the medicinal fluid rises.

5. The calibration system according to claim 1, wherein the two or more conductive plates are rectangular plates coupled to the chamber.

6. The calibration system according to claim 1, wherein the two or more conductive plates are thin wires located along the sides of the chamber.

7. The calibration system according to claim 1, wherein the two or more conductive plates are circular dots coupled to sides of the chamber.

8. The calibration system according to claim 1, wherein the two or more conductive plates are conductive coatings covering a portion of the chamber.

* * * * *